(12) United States Patent
Vogler

(10) Patent No.: US 9,216,110 B2
(45) Date of Patent: Dec. 22, 2015

(54) SYSTEM FOR REFRACTIVE OPHTHALMOLOGICAL SURGERY

(75) Inventor: Klaus Vogler, Eckental (DE)

(73) Assignee: WaveLight GmbH, Erlangen (DE)

( * ) Notice: Subject to any disclaimer, the term of this patent is extended or adjusted under 35 U.S.C. 154(b) by 494 days.

(21) Appl. No.: 12/937,351

(22) PCT Filed: Apr. 3, 2009

(86) PCT No.: PCT/EP2009/002483
§ 371 (c)(1),
(2), (4) Date: Jan. 21, 2011

(87) PCT Pub. No.: WO2009/124695
PCT Pub. Date: Oct. 15, 2009

(65) Prior Publication Data
US 2011/0144628 A1  Jun. 16, 2011

(30) Foreign Application Priority Data
Apr. 11, 2008 (EP) .................................... 08007250

(51) Int. Cl.
*A61F 9/01* (2006.01)
*A61F 9/008* (2006.01)

(52) U.S. Cl.
CPC ............. *A61F 9/008* (2013.01); *A61F 9/00804* (2013.01); *A61F 9/00836* (2013.01); *A61F 2009/00846* (2013.01); *A61F 2009/00851* (2013.01); *A61F 2009/00872* (2013.01)

(58) Field of Classification Search
CPC ............ A61F 2009/00872; A61F 2009/00882; A61F 9/00804; A61F 2009/00851; A61F 9/008; A61F 9/00836; A61F 2009/00846; A61B 3/102
See application file for complete search history.

(56) References Cited

U.S. PATENT DOCUMENTS

| | | | | |
|---|---|---|---|---|
| 5,098,426 | A * | 3/1992 | Sklar et al. ......................... | 606/5 |
| 2007/0073905 | A1 | 3/2007 | Cynthia et al. | |
| 2007/0076217 | A1* | 4/2007 | Baker et al. .................... | 356/498 |
| 2007/0282313 | A1 | 12/2007 | Huang et al. | |
| 2008/0058781 | A1 | 3/2008 | Langeweyde et al. | |
| 2009/0131921 | A1* | 5/2009 | Kurtz et al. ........................ | 606/4 |
| 2010/0049180 | A1* | 2/2010 | Wells et al. ..................... | 606/12 |

(Continued)

FOREIGN PATENT DOCUMENTS

| | | |
|---|---|---|
| DE | 10323422 | 4/2004 |
| EP | 0697611 | 2/1996 |

(Continued)

OTHER PUBLICATIONS

Schoen ("Long-wavelength dilute nitride VECSELs and SESAMs", Mar. 2007).*
Office Action received in corresponding Canadian Patent Application No. 2,721,113, dated Oct. 18, 2012, 2 pages.

*Primary Examiner* — Gary Jackson
*Assistant Examiner* — Scott T Luan
(74) *Attorney, Agent, or Firm* — Haynes and Boone, LLP

(57) ABSTRACT

A system for refractive ophthalmological surgery, in particular LASIK, has—in addition to the ablation laser and, where appropriate, further optical guidance means (18, 30)—a device (34) for optical coherence tomography as an integrated component, in order to make available results of measurement acquired with this device either for the purpose of representation on a display device and/or for the purpose of control of the ablation.

19 Claims, 2 Drawing Sheets

(56) References Cited

U.S. PATENT DOCUMENTS

2010/0324543 A1* 12/2010 Kurtz et al. .................. 606/6
2011/0116040 A1* 5/2011 Biernat et al. ............... 351/206

FOREIGN PATENT DOCUMENTS

| EP | 1231496 | 8/2002 |
| WO | WO 2006/087180 | 8/2006 |

* cited by examiner

SYSTEM FOR REFRACTIVE OPHTHALMOLOGICAL SURGERY

CROSS REFERENCE

This application was originally filed as Patent Cooperation Treaty Application Number PCT/EP2009/002483 on Apr. 3, 2009 and claims priority of European Application Number 08007250.7, filed Apr. 11, 2008.

CROSS-REFERENCE TO RELATED APPLICATION

This application is a United States national phase application of co-pending international patent application number PCT/EP2009/002483, filed Apr. 3, 2009, the disclosure of which is incorporated herein by reference.

BACKGROUND

The invention relates to a system for refractive ophthalmological surgery.

In refractive ophthalmological surgery the optical refractive properties of the eye, particularly of the cornea, are changed by using laser radiation in order to correct or at least alleviate visual deficiencies. A prominent example of refractive ophthalmological surgery is LASIK, in which corneal tissue is resected (ablated) in order to reshape the cornea for the purpose of correcting sight defects. For the purpose of resecting corneal tissue, as a rule an excimer laser in the UV region (typically 193 nm) is employed. The laser radiation is guided over the eye in such a way with respect to time and location that a certain amount of tissue is resected at selected points in the cornea. This resection is described by the so-called ablation profile, i.e. the ablation profile specifies the resection (ablation) to be performed at each point in the cornea.

The present invention relates, in particular, to LASIK.

The ablation profile is calculated, as a rule, prior to implementation of the surgical intervention in respect of the eye to be corrected. The basis of this calculation is a surveying of the eye in its actual state. For this surveying of the eye, the state of the art is familiar with a variety of techniques, in particular topography-measuring instruments (so-called topolyzers), wavefront analysers, Scheimpflug instruments and also pachymeters.

Refractive ophthalmological surgery with a wavefront analyser or with a topography-measuring instrument is hardly capable of resolving small local structures of the cornea within the millimetre range effectively, let alone of assigning them in defined and locally exact manner, in order to enable a locationally faithful treatment. With topolyzers it is also hardly possible to detect so-called central islands within the millimetre range—that is to say, prominences on the cornea which often originate from preceding, not entirely perfect, operations from the early days of PRK.

At present, attempts are being made to track deviations from the desired ablation process in online manner during the ablation, in particular deviations that are based on a so-called cyclotorsion or on a so-called pupil center shift.

But with these processes that are known at present it is, as a rule, not possible to detect local corneal irregularities precisely and to put the laser beam into effect in the course of such a detection in precisely local manner only at this point, and in the process also to track the outcome of the ablation.

So-called optical coherence tomography has been available for some time as a measuring process for non-contacting surveying of biological tissues, cf. for example B. Wolfgang Drexler, Journal of Biomedical Optics, 9 (1), 42-74, 2004. With optical coherence tomography, in particular using broadband irradiators, it is possible to survey very fine biological structures, in particular with resolutions in the region of 1 μm and finer.

EP 1 231 496 A2 describes the application of optical coherence tomography (OCT) for the controlled alteration of tissue in the eye, the treatment laser being controlled as regards power, exposure-time and spot-size. Treated ocular tissue is distinguished therein from untreated ocular tissue by means of OCT and a threshold value. The region of the ocular tissue that has been successfully treated with the laser is determined with OCT.

US 2007/0282313 A1 (Huang et al.) describes the use of OCT only for the purpose of topographical surveying in refractive surgery. No reference is to be found therein to an online-controlled photoablation by means of OCT. In this state of the art the topographical data acquired with OCT are utilised merely for the advance calculation of an ablation program.

EP 0 697 611 A2 describes a system similar to that of EP 1 231 496 A2, discussed above, with an autofocus system for an ophthalmological surgical microscope. Topographical measurements in respect of the cornea are effected therein, but no online control of a resection of tissue with OCT.

US 2007/0073905 A1 does not use OCT but describes generally the state of the art of a surgical intervention in respect of the eye using previous model calculations.

WO 2006/087180 A2 describes a process for ablation, though without using OCT. DE 103 23 422 A1 also does not describe a use of OCT, but only the detection of an optical pressure range in the tissue.

DETAILED DESCRIPTION

The object underlying the invention is to provide a system of the type stated in the introduction that enables improved surgical outcomes.

To this end, the invention teaches a system for refractive ophthalmological surgery with
  a) first laser for resecting corneal tissue,
  b) means for time-controlled and location-controlled guidance of the radiation of the first laser onto the eye,
  c) a device for optical coherence tomography with a second laser for implementing optical coherence tomography in respect of the eye,
  d) means for time-controlled and location-controlled guidance of the radiation of the second laser onto the eye, and with
  e) a computer which
    e1) in the course of the resection of corneal tissue in accordance with a program controls the first laser and the stated means for time-controlled and location-controlled guidance of the radiation of the first laser onto the eye for the purpose of achieving a reshaping of the cornea,
    e2) controls the device for optical coherence tomography and is programmed in such a way that before the start of, during and after conclusion of the resection of corneal tissue measurements in respect of the cornea are carried out, and
    e3) under specifiable conditions controls the program flow for the resection of corneal tissue subsequent to a measurement by means of optical coherence tomography depending on the result of the measurement.

The invention accordingly integrates a module for optical coherence tomography (OCT) into a system for refractive ophthalmological surgery in such a manner that the results of measurement acquired thereby have an influence, in virtually online manner, on the process of the surgical intervention. In particular, high-resolution and high-speed OCT (HHS-OCT) enables the ascertainment and representation of the corneal structures with resolutions within the µm range at very high speed by virtue of scanning-rates within the range from a few MHz up to several GHz, in particular up to 10 GHz and even up to 100 GHz, and with measuring-times distinctly shorter than one second. Hence it is possible not only to survey the initial structure prior to the resection of corneal tissue and the final structure of the cornea after the resection, but also to track the entire progress of the treatment in between and to control the treatment in a manner depending on results of OCT measurement that are acquired during the treatment.

According to the present invention, a resection of tissue, guided by OCT, is, in particular, effected with a UV laser (typically an excimer laser), in the course of which certain areas of the cornea are targeted and then corneal tissue is resected via a number of shots which are controlled in real time (online) until the OCT measurement in virtually real time (online) yields the desired result of measurement.

By reason of the integration of the OCT module into the system for refractive surgery, it is moreover possible to recognise certain irregularities of the cornea, in particular the so-called central islands, and to take them into account in the treatment. Such central islands—that is to say, irregular prominences on the corneal surface—have dimensions in the region of a few millimetres and less and were therefore barely capable, or not capable, of being registered by conventional measuring methods in the course of refractive surgery. Such irregularities were also not discoverable, or barely discoverable, before or during the treatment, or accurately addressable for the laser control. Corresponding remarks apply in respect of extremely fine irregularities in the form of scars which likewise sometimes arise on the corneal surface.

With broadband optical coherence tomography such irregularities are recognisable, and correspondingly the ablation profile can be formed in such a way that, for example, in the region of central islands (that is to say, prominences on the cornea) locally more corneal tissue is resected in targeted manner than in other regions of the cornea, so that a smooth surface arises overall, whereas in the case of the aforementioned scars the resection in the region of these scars is so greatly reduced that, as a result, a substantially smooth corneal surface likewise arises. If in the state of the art such irregularities were not recognised in the result of measurement and taken in account in the ablation, they were substantially preserved in the course of the ablation and resulted in corresponding irregularities also on or in the treated cornea.

With the integration, according to the invention, of OCT into the system for refractive ophthalmological surgery, it is possible to detect the exact corneal structure as regards cross-section, thickness, anterior surface and posterior surface, and to track it momentarily (instantaneously) during the treatment. Therefore a special configuration of the invention teaches to calculate during the ablation process (that is to say, during the refractive surgery) virtually in real time (online) the respective momentary imaging properties of the cornea such as obtain momentarily by reason of the ablation stage that has been reached, and to conclude the ablation precisely when the imaging properties of the eye that have been calculated online in this way correspond to a desired, specifiable objective. This makes parallel topographical measurements or even wavefront measurements no longer absolutely necessary.

A preferred configuration of the system according to the invention for refractive ophthalmological surgery provides that the computer is programmed in order to represent on a display device results of measurement acquired in the course of optical coherence tomography before and/or during the resection of corneal tissue. In this way the treating physician can inspect virtually in online manner—that is to say, practically in real time—the progress of the ablation, represented graphically. For example, the initial shape of the cornea (before the start of the intervention) can be presented to the physician on the display screen by means of a line (in the case of two-dimensional representation) or by means of a surface (in the case of three-dimensional representation), and then, below that, correspondingly the momentary corneal structure by means of a, for example, colour-contrasted line or surface successively during the intervention. In this connection, in addition the surface of the cornea on the inside of the eye, which is also capable of being surveyed with coherence tomography, can also be optionally indicated to the physician. This helps, in particular, to avoid excessively thin residual thicknesses of the cornea. Further structures of the eye being treated that are of interest, such as the lens and/or the pupil, can also be surveyed with OCT and represented on the display device.

If the aforementioned process is employed in the course of LASIK and if in this case the so-called flap incision is carried out with a femtosecond laser, for example, then the incision arising can be tracked with OCT and represented on the display device, and in the course of the subsequent ablation of corneal tissue the aforementioned lines or surfaces in the graphical representation can be ascertained by computation in such a way that the situation after folding the flap back and after the assumed healing process can be calculated and represented.

Another preferred configuration of the invention provides that an input device is provided, with which a user can cause the computer to bring about an additional resection of corneal tissue with the first laser within a selected range of the represented results of measurement of optical coherence topography, or to reduce the resection of corneal tissue within a selected range.

The invention also teaches the use of extremely fast devices for OCT using femtosecond radiation-sources, preferably with repetition-rates in the region of 10 GHz and preferably in the region of 100 GHz or more, in particular the use of so-called VECSELs or VCSELs (Vertical External Cavity Surface Emitting Lasers). Such semiconductor laser diodes can be pumped electrically or optically and attain very high outputs and efficiencies, despite a physical size within the centimetre range. Femtosecond fibre lasers may also be employed for the invention. The invention also teaches the use of such radiation-sources with generation of fs supercontinua with bandwidths greater than 100 nm up to 1000 nm and with repetition-rates greater than 100 GHz, so that an extremely high measuring-rate can be attained—that is to say, the generation of images of structures of the cornea on, for example, a display screen with an extremely short time-delay in comparison with the state of the cornea actually achieved momentarily in the course of an ablation procedure, i.e. the actual state of the cornea is represented graphically virtually in real time (without time-delay) and may also be processed by computation without time-delay.

Further preferred configurations of the system according to the invention for refractive ophthalmological surgery are described in the dependent claims.

BRIEF DESCRIPTION OF THE DRAWINGS

An exemplary embodiment of the invention will be described in more detail in the following on the basis of the drawings. Shown are:

FIG. 1 shows an eye 10 to be treated by refractive ophthalmological surgery, schematically the cornea 12 thereof, the pupillary margin 14 and a so-called irregularity 16 of the cornea, here in the form of a so-called central island—that is to say, a prominence on the cornea having dimensions within the mm range to μm range.

DETAILED DESCRIPTION"

Figure 1:
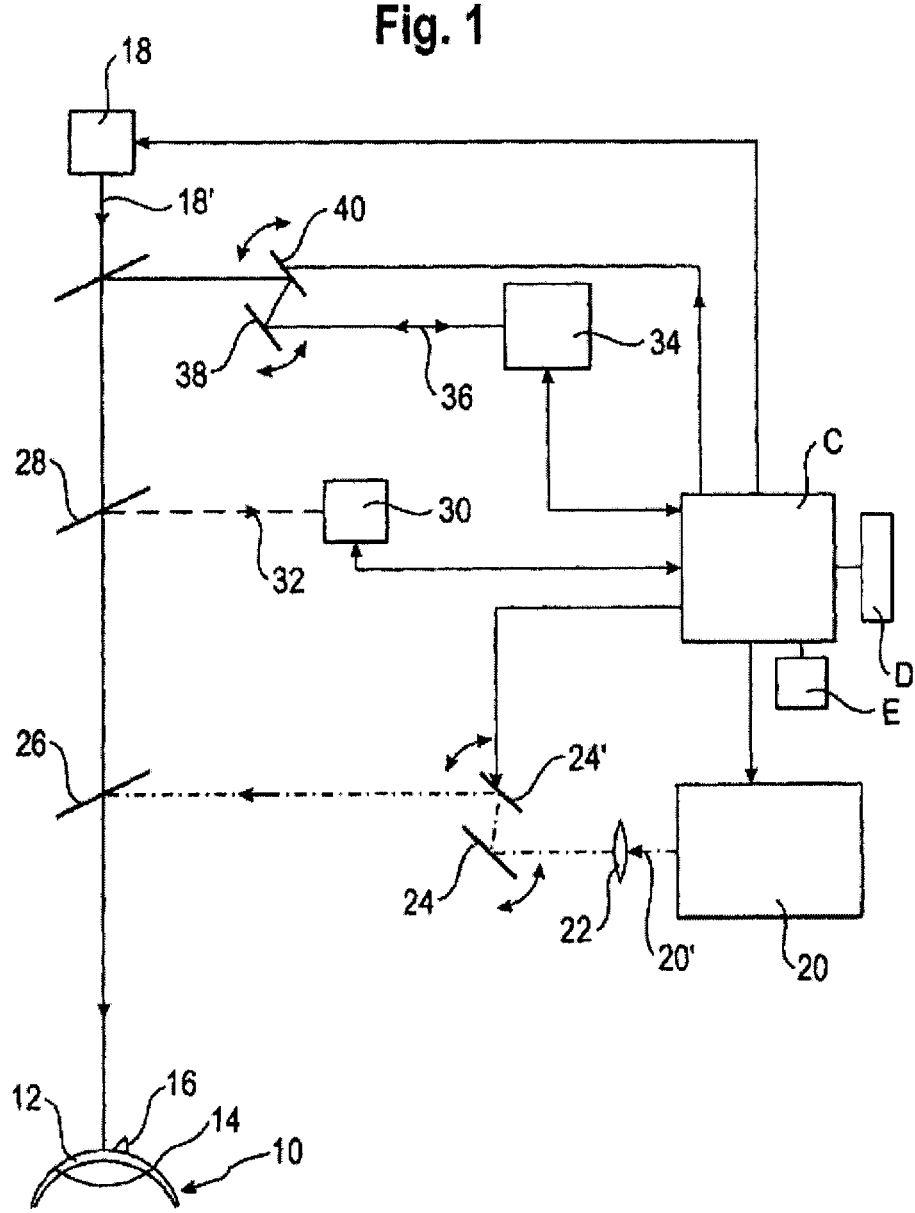
FIG. 1 schematically, a system for refractive ophthalmological surgery.

In known manner the system exhibits a fixation laser 18 which emits a (weak) laser beam 18' and is sighted by the patient for the purpose of fixing the eye.

In a manner known as such, the system exhibits—as in the case of a LASIK apparatus—a UV laser 20, for example an excimer laser, which emits radiation 20' with a wavelength of 193 nm which is directed onto scanner mirrors 24, 24' via a lens 22 and is deflected onto the eye 10 via a deflecting mirror 26. A computer C controls the laser 20 and the scanner mirrors 24, 24', in a manner conventional as such, in accordance with a previously calculated ablation profile. With the system that has been presented, a LASIK, for example, is carried out in known manner.

The system exhibits moreover a so-called eye-tracker. The eye-tracker includes a camera 30 with which images from the eye 10 in the direction of the arrow 32 are recorded via a deflecting mirror 28, which are then subjected to image processing in a manner known as such, in order to track movements of the eye which the patient frequently cannot avoid, despite the fixation laser 18, and to track the control of the scanner mirrors 24, 24' for the laser beam 20' in a manner corresponding to the movements of the eye, so that the ablation profile is resected in a manner that is as locationally faithful as possible.

The digitally acquired recordings of the camera 30 are processed in the computer C, and the computer C then controls the scanner mirrors 24, 24' correspondingly with respect to the ablation beam 20'.

Integrated into the system for LASIK is a device 34 for optical coherence tomography, which in a manner known as such includes an appropriate laser. The device 34 for optical coherence tomography emits radiation and receives radiation in accordance with the double-headed arrow 36. The scanning is effected via scanner mirrors 38, 40. The interaction of the computer C with the individual components is indicated in FIG. 1 by lines and arrows. Correspondingly, the computer C controls the device 34 for optical coherence tomography and the scanner mirrors 38, 40 pertaining thereto.

The device 34 for optical coherence tomography operates with scanning-rates in the region of a few MHz up to scanning-rates within the GHz range, depending on the radiation-source being used, so that measuring-times for an entire surface to be surveyed (that is to say, corresponding roughly to the ablation region of the cornea) are attained that are distinctly shorter than 1 second.

The radiation-source of the device 34 for optical coherence tomography—for example, a laser—is an extreme broadband radiation-source with a broadband measure distinctly greater than 100 nm and with very high repetition-rates greater than 10 MHz up to more than 100 GHz. This enables a high three-dimensional resolution in the region of 10 μm and better. In this case, an image of interest of a surface of the cornea—for example, the momentary surface during the successive ablation—can be surveyed in less than 1 second and can be represented on a display device D via the computer C. The broadband radiation with $\Delta\lambda \gg 100$ nm has centre wavelengths $\lambda$ in the region of about 800 nm to 1300 nm. Hence, according to the exemplary embodiment that is shown, the topography of the cornea, the thickness thereof, the extent of the anterior chamber of the eye and the local position of the adjoining structures—such as iris and crystalline lens—are surveyed, and corresponding geometrical images of these structures are represented, alternatively and in desired combination, on the display device D via the computer C.

The resolution in depth (ordinarily designated as the z-direction) in this case lies within the μm range, for example better than 3 μm, whereas in the transverse direction (ordinarily designated as the xy-direction) resolutions distinctly better than 10 μm are likewise attained. Hence substructures of the cornea—such as the epithelium, Bowman's membrane, or the position of the microkeratome incision in the case of LASIK—can be recognised well.

Figure 2:
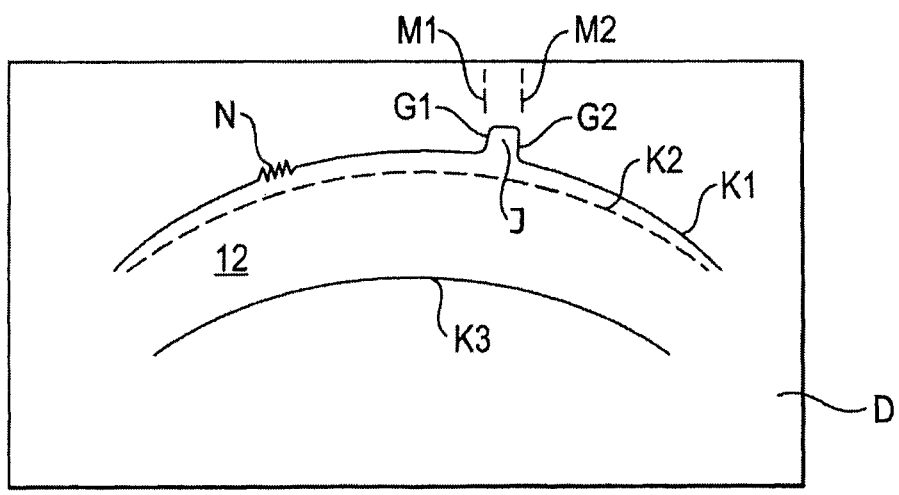
FIG. 2 schematically, a display device for displaying data acquired with optical coherence tomography.

FIG. 2 shows schematically a representation with OCT-surveyed structures on the display device D in accordance with a control by the computer C. Shown is the surface K1 of the cornea obtaining before the start of the ablation, with a first irregularity I in the form of a central island—that is to say, a prominence. The prominence has dimensions within the mm range to μm range (is accordingly extremely enlarged in the Figure in comparison with the dimensions of the cornea). The two flanks of the prominence have gradients G1, G2, i.e. slopes in relation to the adjoining surface K1 of the cornea 12. Moreover, in the example that is represented the surface K1 of the cornea 12 has scars N which likewise have dimensions within the mm range to μm range.

Moreover, FIG. 2 shows the set surface K2 of the cornea to be striven for on the basis of the calculated resection of the ablation profile—that is to say, the outcome of the operation to be striven for. FIG. 2 also shows the inner surface K3 of the cornea schematically.

With the device 34 for optical coherence tomography and with the computer C which processes the results of measurement of said device, the curve K1 according to FIG. 2 can be generated and can be represented on the display device D. In this connection the computer C is programmed in such a way that it recognises the stated irregularities having dimensions within the μm range and, according to an option of the user, represents them in emphasised manner, for example in colour or by means of thick lines. With processes of image processing that are known as such, the computer can 'recognise' the irregularities on the basis of the gradients G1, G2 by comparison with specifiable threshold values and can represent them. In the course of image processing, for example, by comparison of contiguous measuring-point ranges a gradient G1, G2 can be recognised that lies above a specified threshold value and indicates that an irregularity is possibly present at this point. According to a preferred configuration, the option can then be made available to the user to call up and represent an enlarged representation of the momentary state of the cornea in this critical region. This representation can be continually repeated online during the implementation of the ablation—that is to say, during the stepwise resection of corneal tissue, layer by layer—so that the physician can track the progress of the treatment—i.e. the temporal procedure of the successive resection of corneal tissue, layer by layer—on the display device D on the basis of the measurements by coherence tomography. If on the basis of the irregularities the physician detects certain problem regions in which a stronger ablation or even a weaker ablation than originally stipulated in accordance with the ablation profile is required, then according to a preferred configuration he/she can intervene in the process directly. If, for example, the physician detects on the representation an irregularity corresponding to the prominence I (central island), then he/she can place markers M1 M2, between which in this case an increased resection of corneal tissue in comparison with the surrounding regions of the cornea is required, and he/she can set the markers M1, M2 corresponding to the delimitation of this region via an input device E. It will be understood that these markers are to be placed three-dimensionally—that is to say, also in the downward direction from the plane of the drawing they have roughly the dimension that is given in the plane of the representation. The physician can then specify via the input device E how strong the additional resection of tissue is to be in the region of the irregularity.

Corresponding remarks apply to the region of the scars N, in which the ablation then has to be diminished where appropriate, in order, as a result, in cases of all irregularities then to obtain a relatively smooth corneal surface as designated by K2 in FIG. 2.

LIST OF REFERENCE SYMBOLS 10 eye
12 cornea
14 pupillary margin
16 scar or central island
18 fixation laser
18' fixation laser beam
20 UV laser
22 lens
24 scanner mirror
24' scanner mirror
26 deflecting mirror
28 deflecting mirror
30 camera
32 arrow
34 OCT system
36 double-headed arrow
38 scanner mirror
40 scanner mirror
C computer
D display
E input
I central island
N scar(s)
M1,M2 markers
G1,G2 gradients
K1,K2,K3,K4 surfaces

What is claimed is:

1. A system for refractive ophthalmological surgery, the system comprising:
    a first laser source producing a pulsed laser beam configured to ablate corneal tissue of an eye to be treated;
    a second laser source associated with an optical coherence tomography ("OCT") module and configured to obtain corneal structure measurements; and
    a computer controller in communication with the first and second laser sources, the computer controller configured to:
        control the OCT module, including the second laser source, to obtain the corneal structure measurements in real time during a procedure;
        control the first laser source such that the pulsed laser beam is guided onto the eye to be treated for the purpose of reshaping at least a portion of a cornea of the eye to be treated to a desired shape in accordance with a desired ablation profile;
        identify a structural irregularity in a surface of the cornea, the structural irregularity comprising a gradient on the surface of the cornea, wherein the identifying includes comparing the gradient to a threshold value;
        output to a display:
            a graphical image representing an initial shape of the cornea of the eye, and
            a graphical image representing a current shape of the cornea of the eye based on the corneal structure measurements obtained by the OCT module in real time during the procedure, wherein the graphical image representing the initial shape of the cornea and the graphical image representing the current shape of the cornea are displayed simultaneously; and
            a graphical image representing the structural irregularity, wherein the graphical image representing the structural irregularity depicts the structural irregularity in an enlarged manner relative the cornea in at least one of the graphical image representing an initial shape of the cornea of the eye or the graphical image representing the current shape of the cornea, wherein the graphical image representing the structural irregularity is selectively displayed in response to identification of the structural irregularity and a user input to view the structural irregularity in an enlarged manner, and wherein the graphical image representing the structural irregularity is updated in real time based on the corneal structure measurements obtained by the OCT module in real time during the procedure while the pulsed laser beam is guided onto the eye; and
        receive, in real time during the procedure, a user input to modify the desired ablation profile;
        wherein the pulsed laser beam is guided onto the eye to be treated based on the corneal structure measurements obtained by the OCT module in real time during the procedure and the user input to modify the desired ablation profile such that the structural irregularities in the eye to be treated are accommodated for to achieve the desired shape.

2. The system of claim 1, wherein the scanning rate is greater than 10 MHz.

3. The system of claim 2, wherein the scanning rate is 10 GHz.

4. The system of claim 1, wherein the first laser source is a femtosecond laser.

5. The system of claim 4, wherein the first laser source is an excimer laser.

6. The system of claim 4, wherein the second laser source is a femtosecond laser source.

7. The system of claim 4, wherein the second laser source is a vertical external cavity surface emitting laser.

8. The system of claim 4, wherein the second laser source has a center wavelength between 800 nm and 1300 nm.

9. The system of claim 1, wherein the initial shape of the cornea output to the display is a two-dimensional representation.

10. The system of claim 1, wherein the initial shape of the cornea output to the display is a three-dimensional representation.

11. The system of claim 1, wherein the computer controller is further configured to recognize μm irregularities in a surface of the cornea.

12. The system of claim 11, wherein the recognized μm irregularities are emphasized relative to other portions of the cornea in the initial shape of the cornea output to the display.

13. The system of claim 11, wherein the computer controller is configured to recognize the μm irregularities in the surface of the cornea by comparing a surface gradient to a threshold value.

14. The system of claim 1, wherein the modification to the desired ablation profile increases tissue resection.

15. The system of claim 1, wherein the modification to the desired ablation profile decreases tissue resection.

16. The system of claim 1, wherein the current shape of the cornea output to the display is displayed in a different color on the display than the initial shape of the cornea output to the display.

17. The system of claim 1, wherein the computer controller also outputs to the display the desired shape of the cornea.

18. The system of claim 1, wherein the user input to modify the desired ablation profile includes identification of an area of the cornea having structural irregularities.

19. The system of claim 18, wherein the user input to modify the desired ablation profile includes positioning markers in at least one of the graphical image representing an initial shape of the cornea of the eye and the graphical image representing the current shape of the cornea to define the area of the cornea having the structural irregularities.

* * * * *